United States Patent [19]

Baudouin et al.

[11] 4,421,918
[45] Dec. 20, 1983

[54] PROCESS FOR THE PREPARATION OF 7-CHLORO-1,2,3,4-TETRAHYDROQUINO-LIN-4-ONE

[75] Inventors: Michel Baudouin, St. Fons; Hubert Linares, Caluire, both of France

[73] Assignee: Rhone-Poulenc Sante, Courbevoie, France

[21] Appl. No.: 339,704

[22] Filed: Jan. 15, 1982

[30] Foreign Application Priority Data

Jan. 16, 1981 [FR] France ............................. 81 00763

[51] Int. Cl.³ .......................................... C07D 215/22
[52] U.S. Cl. .................................................. 546/153
[58] Field of Search ........ 546/153, 49, 56 (U.S. only)

[56] References Cited

U.S. PATENT DOCUMENTS 2,558,211  6/1951  Elderfield et al. .................. 546/153
3,200,122  8/1965  Streiff .................................... 546/56
3,281,836  7/1966  Chen .................................. 546/56 X
3,567,732  3/1971  Joly et al. ....................... 546/153 X

FOREIGN PATENT DOCUMENTS 806715  12/1936  France .
1202105  1/1960  France ............................... 546/153

*Primary Examiner*—Diana G. Rivers
*Attorney, Agent, or Firm*—Stevens, Davis, Miller & Mosher

[57] ABSTRACT

Process for the preparation of 7-chloro-1,2,3,4-tetrahydroquinolin-4-one by cyclizing 3-m-chloroanilinopropionic acid by means of an oleum, and desulphonating the resulting aromatic sulphonic acids by means of dilute sulphuric acid. The quinolinone product is useful as a starting material for the preparation of pharmaceuticals.

4 Claims, No Drawings

PROCESS FOR THE PREPARATION OF 7-CHLORO-1,2,3,4-TETRAHYDROQUINOLIN-4-ONE

DESCRIPTION

The present invention relates to a new process for the preparation of 7-chloro-1,2,3,4-tetrahydroquinolin-4-one of the formula:

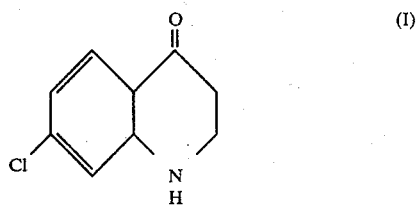

which is a particularly valuable intermediate as it can be used, in particular, for preparing 7-chloro-4-(4-diethylamino-1-methylbutylamino)-quinoline—otherwise known as chloroquine—which is known to possess remarkable antimalarial properties.

It is known, in particular from French Patent 1514280, to prepare 7-chloro-1,2,3,4-tetrahydroquinolin-4-one by cyclising 3-(m-chloroanilino)-propionic acid by means of polyphosphoric acid at a temperature of about 100° C. However, this process has the major disadvantage of leading to a mixture of virtually equal proportions of 5-chloro-1,2,3,4-tetrahydroquinolin-4-one and 7-chloro-1,2,3,4-tetrahydroquinolin-4-one, the constituents of which mixture must be separated in order for them to be used subsequently.

It is also known from French Patent No. 806715 to prepare the aforesaid quinolin-4-one by cyclising a 3-arylaminopropionitrile unsubstituted on the nitrogen by operating in the presence of aluminium chloride; the cyclisation can be carried out using other agents such as boron trifluoride, aluminium bromide, the halides of titanium, tin, arsenic or antimony, or the oxyhalides of phosphorus (POCl$_3$), or ferric chloride, or hydrogen halides or sulphuric acid.

It has now been found that 7-chloro-1,2,3,4-tetrahydroquinolin-4-one of formula (I) can be prepared with good yields and virtually free of the 5-chloro isomer by cyclising 3-m-chloroanilinopropionic acid in an oleum at a temperature between 0° and 40° C. and then desulphonating the resulting intermediate aromatic sulphonic acids of the formula:

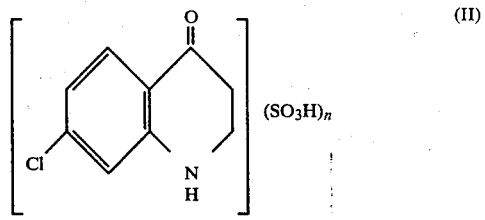

(where n is 1 or 2) by means of dilute sulphuric acid at a temperature between 120° and 180° C.; it is this finding which forms the subject of the present invention.

The cyclisation of the 3-m-chloroanilinopropionic acid is preferably carried out in an oleum containing 20% of sulphur trioxide; however, it is possible to use a more concentrated oleum (70%) but in such a case the results are generally less satisfactory.

It is particularly advantageous if the concentration of the 3-m-chloroanilinopropionic acid in the oleum, at the start of the reaction, is of the order of 10% (w/v). When using 20% oleum, the concentration of sulphur trioxide is of the order of 4.7 mols/liter and the molar ratio sulphur trioxide/m-chloroanilinopropionic acid is about 9. However, good results are still obtained with higher concentrations of 3-m-chloroanilinopropionic acid (20% w/v) and with a lower molar ratio sulphur trioxide/m-chloroanilinopropionic acid, e.g. of the order of 5; ratios of between 5 and 10 are suitable.

The cyclisation of the 3-m-chloroanilinopropionic acid is preferably carried out at a temperature of about 20° C. for 12 to 16 hours. However, good yields are still obtained when carrying out the reaction at a lower temperature, e.g. 0° C., with a longer reaction time, e.g. from 60 to 70 hours.

The desulphonation of the aromatic sulphonic acid intermediates can be carried out, after dilution of the reaction medium with water, by heating at a temperature between 120° and 180° C. If the concentration of sulphuric acid in the reaction mixture is about 70%, the desulphonation is complete after a heating time of about 30 minutes at 145° C.; if the concentration is about 55%, the heating time is from 8 to 20 hours, preferably 16 hours, at the same temperature.

The 7-chloro-1,2,3,4-tetrahydroquinolin-4-one is separated from the reaction mixture, after dilution with water, in accordance with the usual methods, e.g. by extraction with a suitable organic solvent such as methylene chloride or chlorobenzene.

7-Chloro-1,2,3,4-tetrahydroquinolin-4-one can be converted to chloroquine by condensing it with 4-diethylamino-1-methylbutylamine in the presence of air, in accordance with the process described by W. S. Johnson and B. G. Buell, J. Amer. Chem. Soc., 74, 4513 (1952).

The 3-m-chloroanilinopropionic acid used as a starting material is obtained by reacting m-chloroaniline with acrylic acid.

The reaction is carried out in water at a temperature between 90° and 100° C., using an excess of m-chloroaniline relative to the acrylic acid used. The reaction time is of the order of 1 hour.

The following Examples, which are given without implying a limitation, illustrate the way in which the process according to the invention is carried out.

EXAMPLE 1

A 250 cc three-necked, round-bottom flask, fitted with a stirrer and a reflux condenser surmounted by an argon inlet, is placed in a bath thermostated at 20° C. The apparatus is purged with argon and 20% oleum (containing 0.470 mol of SO$_3$ and 1.534 mols of H$_2$SO$_4$; 188 g) is introduced. This is stirred for 30 minutes to bring the temperature to 20° C. 3-m-Chloroanilinopropionic acid (10.146 g; 5.086×10$^{-2}$ mols) is then introduced in small portions in the course of 5 minutes. The temperature rises to 24.5° C. and then drops to 20° C. again in the course of 10 minutes. The reaction mixture is stirred for 16 at 20° C., after which it is poured onto ice (88.6 g) in such a way that the temperature does not exceed 25° C.

The solution is then heated for 30 minutes at a temperature between 138° and 140° C. under an argon atmosphere. After cooling, the reaction mixture is poured onto ice (420 g). The yellow solution obtained is extracted with methylene chloride (100 cc) and then with the same solvent again (5×50 cc). A gummy, insoluble material is filtered off. The methylene chloride solution is washed with a saturated solution of sodium chloride (2×25 cc), then with a 2N solution of sodium hydroxide (7×25 cc) and finally with a saturated solution of sodium chloride (5×25 cc), and is then dried over sodium sulphate, treated with decolorising charcoal and finally filtered. After the solvent has been evaporated off, 7-chloro-1,2,3,4-tetrahydroquinolin-4-one (7.535 g) is obtained in the form of a crystalline product melting at 133° C. (Kofler bench).

The degree of conversion is 100% and the yield is 81.6%.

The proportion of the 5-chloro isomer is estimated by thin layer chromatography to be 2.5%.

The starting 3-m-chloroanilinopropionic acid can be prepared in the following manner:

A mixture of m-chloroaniline (50 g; 0.392 mol) and acrylic acid (14.1 g; 0.195 mol) in distilled water (25 cc), kept under a nitrogen atmosphere, is stirred for 1 hour at 95° C. After cooling, the aqueous phase is decanted. The organic layer is washed three times with distilled water (500 cc in total), diluted by adding diethyl ether (100 cc) and then extracted with 2N sodium hydroxide solution (100 then 200 cc). The basic aqueous extracts are combined and washed four times with diethyl ether (300 cc in total).

The various ether extracts are combined, washed with distilled water (50 cc) and then dried over sodium sulphate. After filtration and evaporation of the solvent, chromatographically pure m-chloroaniline (24.7 g) is recovered.

The basic aqueous extracts previously separated are acidified to pH 3.5 by adding concentrated hydrochloric acid (20 cc). The oil which settles out is separated off and the aqueous phase is extracted with benzene (200 cc). The oil which settled out and the benzene phase are combined and washed twice with distilled water (100 cc in total); the organic phase thus obtained is dried over sodium sulphate. After filtration, the solvent is evaporated off under reduced pressure and the residue is heated for 1 hour at 70° C. under a pressure of 18 mm Hg so as to remove all the solvent. After cooling, this yields 3-m-chloroanilinopropionic acid (35.1 g), which crystallises very slowly on standing.

The degree of conversion of the m-chloroaniline is 100% and the yield (relative to the m-chloroaniline consumed) is 87.7%.

EXAMPLE 2

Pure sulphuric acid (147.7 g.), contained in a 500 cc round-bottomed flask purged with argon beforehand and fitted with a stirrer, is heated to 45° C. 3-m-Chloroanilinopropionic acid (52.55 g) is then added in small portions, whilst stirring and keeping the temperature at between 43° and 45° C. When all the 3-m-chloroanilinopropionic acid has dissolved, the reaction mixture is cooled to 20° C. and oleum (216.5 g) containing 65.2% of sulphur trioxide is then added slowly in the course of 2½ hours, whilst stirring vigorously and keeping the temperature at 20° C. The reaction is then continued for 20 hours at 20° C.

Water (181.9 g) is then added slowly in the course of 1 hour 20 minutes, whilst stirring and cooling so as to keep the temperature of the reaction mixture between 18° and 20° C.

The reaction mixture thus obtained (562.2 g) is heated at 143° C. for 50 minutes. After rapid cooling to 50° C., water (359.7 g) is added rapidly to the reaction mixture. The temperature rises to 75° C. The mixture is then extracted with chlorobenzene (4×250 cc), the temperature being kept between 75° and 80° C. The combined organic phases are washed with a 1N aqueous solution of sodium hydroxide (2×100 cc) and then with water (3×100 cc). The chlorobenzene is evaporated off under reduced pressure. This yields a crude product (34.75 g), which is shown by gas phase chromatographic analysis to contain 93% of 7-chloro-1,2,3,4-tetrahydroquinolin-4-one and 4.4% of 5-chloro-1,2,3,4-tetrahydroquinolin-4-one.

The degree of conversion of the 3-m-chloroanilinopropionic acid is more than 99.4% and the yield of 7-chloro-1,2,3,4-tetrahydroquinolin-4-one is 76% relative to the 3-m-chloroanilinopropionic acid used.

We claim:

1. A process for the preparation of 7-chloro-1,2,3,4-tetrahydroquinolin-4-one which comprises cyclising 3-m-chloroanilinopropionic acid by means of an oleum, then desulphonating the intermediate aromatic sulphonic acids of the formula:

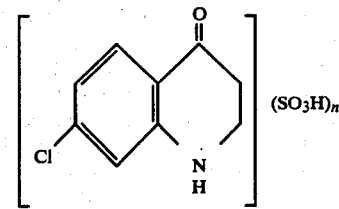

(wherein n is 1 or 2) by means of dilute sulphuric acid, and then isolating the 7-chloro-1,2,3,4-tetrahydroquinolin-4-one obtained.

2. A process according to claim 1 in which the cyclisation is carried out by means of an oleum containing 10 to 70% of sulphur trioxide, the reaction being carried out at a temperature between 0° and 40° C.

3. A process according to claim 1 in which the molar ratio sulphur trioxide/3-m-chloroanilinopropionic acid at the start of the cyclisation is between 5 and 10.

4. A process according to claim 1 in which the desulphonation is carried out, after dilution of the reaction mixture in water, by heating at a temperature between 120° and 180° C.

* * * * *